(12) United States Patent
Chalyt et al.

(10) Patent No.: US 6,733,656 B2
(45) Date of Patent: May 11, 2004

(54) VOLTAMMETRIC REFERENCE ELECTRODE CALIBRATION

(75) Inventors: Gene Chalyt, Washington Township, NJ (US); Peter Bratin, Flushing, NY (US); Michael Pavlov, Fairlawn, NJ (US); Alex Kogan, Carlstadt, NJ (US); Michael James Perpich, Hackensack, NJ (US)

(73) Assignee: ECI Technology Inc., East Rutherford, NJ (US)

( * ) Notice: Subject to any disclaimer, the term of this patent is extended or adjusted under 35 U.S.C. 154(b) by 231 days.

(21) Appl. No.: 10/115,539

(22) Filed: Apr. 3, 2002

(65) Prior Publication Data

US 2003/0188977 A1 Oct. 9, 2003

(51) Int. Cl.$^7$ .............................................. G01N 27/48
(52) U.S. Cl. ........................... 205/775; 205/81; 204/434
(58) Field of Search ........................... 204/228.6, 229.1, 204/230.2, 401, 434, 435; 205/775, 789, 81

(56) References Cited

FOREIGN PATENT DOCUMENTS

WO          WO 99/57340 A2  * 11/1999   ............. C25D/1/00

* cited by examiner

*Primary Examiner*—Alex Noguerola
(74) *Attorney, Agent, or Firm*—D. Morgan Tench

(57) ABSTRACT

In the present invention, the test reference electrode used for voltammetric analysis of a plating bath is calibrated relative to the zero-current point between metal plating and stripping at a rotating platinum disk electrode in the plating bath supporting electrolyte. This calibration is readily performed during the normal course of cyclic voltammetric stripping (CVS) or cyclic pulse voltammetric stripping (CPVS) plating bath analysis the need for additional instrumentation or removal of the test reference electrode from the analysis equipment. Automatic calibration of the reference electrode enabled by the present invention, saves labor, time and expense, and minimizes errors in the plating bath analysis.

22 Claims, 2 Drawing Sheets

VOLTAMMETRIC REFERENCE ELECTRODE CALIBRATION

CROSS-REFERENCE TO RELATED APPLICATIONS

This application is related to U.S. patent application Ser. No. 09/968,202, filed Oct. 1, 2001, to Chalyt et al., which is assigned to the same assignee.

BACKGROUND OF THE INVENTION

1. Field of the Invention

This invention is concerned with analysis of organic additives and other components of plating baths as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level or brighten the deposit by suppressing the electrodeposition rate at peaks in the substrate surface. Leveling/brightening of the deposit results from faster metal deposition within recessed areas where the additive, which is present at low concentration, is less effectively replenished by diffusion/bath agitation as it is consumed in the electrodeposition process. The most sensitive methods available for detecting leveling and brightening additives in plating baths involve electrochemical measurement of the metal electrodeposition rate under controlled hydrodynamic conditions for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in the plating bath between fixed potential limits so that metal is alternately plated on and stripped from the electrode surface. Such voltage cycling is designed to establish a steady state for the electrode surface so that reproducible results are obtained. Cyclic pulse voltammetric stripping (CPVS), also called cyclic step voltammetric stripping (CSVS), is a variation of the CVS method that employs discrete changes in voltage during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

Accumulation of organic films or other contaminants on the electrode surface can be avoided by periodically voltage cycling the electrode in the plating solution without organic additives and, if necessary, polishing the electrode using a fine abrasive. The metal deposition rate can be determined from the current or charge passed during metal electrodeposition but it is usually advantageous to measure the charge associated with anodic stripping of the metal from the electrode. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52 (1981) and Plating Surf. Fin. 69(3), 62 (1982)].

Acid copper sulfate electroplating baths require a minimum of two types of organic additives to provide deposits with satisfactory properties and good leveling characteristics. The suppressor additive is typically a polymeric organic species, e.g., high molecular weight polyethylene or polypropylene glycol, which adsorbs strongly on the copper cathode surface to form a film that sharply increases the overvoltage for copper deposition. This prevents uncontrolled copper plating that would result in powdery or nodular deposits. An anti-suppressor additive is required to counter the suppressive effect of the suppressor and provide the mass-transport-limited rate differential needed for leveling. Plating bath vendors typically provide additive solutions that may contain additives of more than one type, as well as other organic and inorganic addition agents. The suppressor additive may be comprised of more than one chemical species and generally involves a range of molecular weights.

Both the suppressor and the anti-suppressor additive concentrations in acid copper sulfate baths can be determined by CVS analysis methods based on the effects that these additives exert on the copper electrodeposition rate. For the suppressor analysis, the CVS rate parameter, usually the copper stripping peak area at a given electrode rotation rate ($A_r$), is first measured in a supporting electrolyte having approximately the same composition as the plating bath to be analyzed but without organic addition agents. Additions of known volume ratios of the plating bath to the supporting electrolyte (or to a background electrolyte having known concentrations of other additives) produce decreases in the CVS rate parameter that reflect the concentration of the suppressor additive. This "standard addition" suppressor analysis is not significantly affected by the presence of the anti-suppressor, which exerts a relatively weak effect on the copper deposition rate at the plating bath dilution levels involved. For the anti-suppressor analysis, a sufficient amount of the suppressor additive, which may be comprised of a plurality of components or species, is added to the supporting electrolyte to produce a background electrolyte exhibiting substantially the maximum suppression of the copper deposition rate (minimum CVS rate parameter). Additions of known volume ratios of the plating bath to this fully-suppressed background electrolyte produce increases in the CVS rate parameter that can be related to the concentration of the anti-suppressor additive. The exact procedures for CVS analysis of acid copper sulfate baths can vary.

Analysis for the suppressor additive (also called the "polymer", "carrier", or "wetter", depending on the bath supplier) typically involves generation of a calibration curve by measuring the CVS rate parameter $A_r$ in a supporting or background electrolyte (without organic additives or with known concentrations of interfering additives), termed $A_r(0)$, and after each standard addition of the suppressor additive. For the calibration curve, $A_r$ may be plotted against the suppressor concentration directly, or normalized as $A_r/A_r(0)$ to minimize measurement errors associated with changes in the electrode surface, background bath composition, and temperature. For the suppressor analysis itself, $A_r$ is first measured in the supporting electrolyte and then after each standard addition of a known volume ratio of the plating bath sample to be analyzed. The suppressor concentration may be determined from the $A_r$ or $A_r/A_r(0)$ value for the measurement solution (supporting electrolyte plus a known volume of plating bath sample) by interpolation with respect to the appropriate calibration curve ("response curve analysis"). Alternatively, the suppressor concentration may be determined by the "dilution titration" method from the volume ratio of plating bath sample (added to the supporting electrolyte) required to decrease $A_r$ or $A_r/A_r(0)$ to a given value, which may be a specific numerical value or a minimum value (substantially maximum suppression) [W. O. Freitag, C. Ogden, D. Tench and J. White, Plating Surf. Fin. 70(10), 55 (1983)]. Note that the effect of the anti-suppressor on the suppressor analysis is typically small but can be taken into account by including in the background electrolyte the amount of anti-suppressor measured or estimated to be present in the plating bath being analyzed.

The concentration of the anti-suppressor additive (also called the "brightener", "accelerator" or simply the "additive", depending on the bath supplier) is typically determined by the linear approximation technique (LAT) or modified linear approximation technique (MLAT) described by R. Gluzman [Proc. $70^{th}$ Am. Electroplaters Soc. Tech. Conf., Sur/Fin, Indianapolis, Ind. (June 1983)]. The CVS rate parameter, $A_r$, is first measured in background electrolyte containing no anti-suppressor but with a sufficient amount of suppressor species added to substantially saturate suppression of the copper deposition rate. A known volume ratio of the plating bath sample to be analyzed is then added to this fully-suppressed background electrolyte and $A_r$ is again measured. The $A_r$ measurement is then repeated in this mixed solution after each addition (typically two) of known amounts of the anti-suppressor additive only. The concentration of the anti-suppressor in the plating bath sample is calculated assuming that $A_r$ varies linearly with anti-suppressor concentration, which is verified if the change in $A_r$ produced by standard additions of the same amount of anti-suppressor are equivalent.

Acid copper sulfate baths have functioned well for plating the relatively large surface pads, through-holes and vias found on printed wiring boards (PWB's) and are currently being adapted for plating fine trenches and vias in dielectric material on semiconductor chips. The electronics industry is transitioning from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p. 32; U.S. Pat. No. 4,789,648 to Chow et al.; U.S. Pat. No. 5,209,817 to Ahmad et al.), which depends on copper electroplating to provide complete filling of the fine features involved. The organic additives in the bath must be closely controlled since they provide the copper deposition rate differential required for bottom-up filling.

As the feature size for the Damascene process has shrunk below 0.2 $\mu$m, it has become necessary to utilize a third organic additive in the acid copper bath in order to avoid overplating the trenches and vias. Note that excess copper on Damascene plated wafers is typically removed by chemical mechanical polishing (CMP) but the copper layer must be uniform for the CMP process to be effective. The third additive is called the "leveler" (or "booster", depending on the bath supplier) and is typically an organic compound containing nitrogen or oxygen that also tends to decrease the copper plating rate. In order to attain good bottom up filling and avoid overplating of ultra-fine chip features, the concentrations of all three additives must be accurately analyzed and controlled.

The concentrations of the suppressor and anti-suppressor in acid copper plating baths can be analyzed with good precision in the presence of the leveler additive by the standard CVS methods. At the additive concentrations typically employed, the effect of the suppressor in reducing the copper deposition rate is usually much stronger than that of the leveler so that the concentration of the suppressor can be determined by the usual CVS response curve or dilution titration analysis. Interference from the leveler can be minimized by utilizing a background electrolyte for the suppressor analysis that contains approximately the same leveler concentration as in the plating bath being analyzed, estimated from the bath makeup composition and previous analyses. Likewise, the anti-suppressor concentration can be determined by the LAT or MLAT analysis procedure and the approximate bath concentration of leveler can be added to the fully-suppressed background electrolyte to minimize leveler interference. With some modifications, for example, to account for relatively high leveler activity or to reduce anti-suppressor interference on the suppressor analysis, these CVS procedures provide reliable measures of the suppressor and anti-suppressor additives used in currently-available acid copper electroplating baths. In addition, a method for measuring the leveler concentration in the presence of interference from both the suppressor and anti-suppressor was described in U.S. patent application Ser. No. 09/968,202, filed Oct. 1, 2001, to Chalyt et al., which is assigned to the same assignee as the present application.

For CVS and other voltammetric bath analysis methods based on measurements of the metal electrodeposition rate, the electrode potential must be precisely controlled. This is normally accomplished by use of a reference electrode in conjunction with an electronic potentiostat. However, the potential of commercially available reference electrodes tends to drift with time, especially as plating bath chemicals diffuse into the reference electrode solution. Some commercial reference electrodes employ gelled electrolytes to inhibit diffusion of contaminants but such electrodes exhibit significant potential drift both under storage conditions and in contact with plating baths. Reference electrode voltage drift can introduce large errors in measured metal deposition rate parameters. For example, a small change in the cathodic potential limit, at which the metal deposition current is highest, has a large effect on the overall amount of metal deposited and consequently on the metal stripping peak areas typically used for CVS and CPVS additive analyses. Likewise, the cathodic current associated with metal deposition typically increases sharply with increased cathodic potential in the region of interest for voltammetric bath analysis so that a small error in measured electrode potential has a large effect on the measured current.

The normal procedure for handling reference electrode drift is to replace the test reference electrode or make corrections to the measured potential based on periodic calibration of the test reference electrode against that of a standard reference electrode. Such calibration involves placing the two electrodes in contact with an electrolyte and measuring the potential difference using a high-impedance voltmeter. Ideally, the two reference electrodes are of the same type and the electrolyte used for the calibration is the same as that in the electrodes so that junction potentials and contamination of the solution in the standard reference are avoided. Alternatively, contamination by plating bath species can be minimized by bringing the standard reference electrode into contact with the plating bath or the supporting electrolyte for only brief periods of time.

Use of a standard reference electrode for calibration of the test electrode generally involves periodic removal of the test electrode from the analysis equipment or insertion of the standard reference electrode in a plating solution in the analysis equipment, which are typically manual operations that are time-consuming and costly. In addition, periodic calibration against another standard reference electrode is needed to ensure that the potential of the standard reference electrode used to calibrate the test electrode remains constant. Interruption of bath analysis during the time required for reference electrode calibration or changeout of reference electrodes can also present a problem, particularly for automated on-line analysis equipment designed to provide very close control of critical electroplating process parameters. Access to the reference electrode in such automated equipment is often not very good, rendering calibration more difficult and time consuming. The only approach currently available for addressing these problems is to use complicated equipment that automatically changes the solution in the reference electrode.

There is an important need for a method of calibrating reference electrodes used for plating bath analyses that does not require removal of the electrode from the plating equipment and can be performed automatically and quickly without complicated equipment. In addition to saving labor, time and expense, such a method would make frequent reference electrode calibration practical so that measurement errors could be minimized.

SUMMARY OF THE INVENTION

The present invention is a method of calibrating the reference electrode used for voltammetric analysis of a plating bath. In this method, an inert working electrode and the reference electrode are brought into contact with the supporting electrolyte of the plating bath (or the plating bath itself or a background electrolyte) and the potential of the working electrode is changed as a function of time relative to the potential of the reference electrode such that metal is plated onto and then anodically stripped from the working electrode surface. The current response to the potential of the working electrode is monitored and the potential corresponding to a selected stage in the current response is used to calibrate the reference electrode potential. The calibration is preferably performed using the supporting electrolyte rather than the plating bath or a background electrolyte to avoid interference from plating bath additives.

Various stages in the current response are apparent in plots of current versus working electrode potential. The key features of such voltammograms are the cathodic current associated with metal plating and an anodic peak associated with substantially complete stripping of the metal from the working electrode surface. The stage of the current response used for the calibration is selected such that the corresponding working electrode potential is substantially independent of normal variations in the supporting electrolyte composition and temperature. A preferred stage in the current response for reference electrode calibration is the zero-current crossover from metal plating to metal stripping but other current stages may also be used.

In a preferred embodiment, the working electrode is an inert metal (platinum, for example) in the well-known rotating disk configuration and is rotated (typically at a constant rate) to control solution mass transport so as to provide more reproducible results. Also, it is usually advantageous to use a counter electrode and an electronic potentiostat to control the potential of the working electrode relative to the reference electrode. This approach avoids passing appreciable current through the reference electrode, which could polarize the reference electrode and change its potential. In some cases, especially when the currents involved are relatively small, the reference electrode may also serve as the counter electrode so that a separate counter electrode is not needed. In one embodiment, the potential of the working electrode relative to the reference electrode is cycled at a constant rate between fixed negative and positive potential limits, as in the CVS bath analysis method, but other voltage waveforms may be used. For example, the working electrode potential may be scanned in some potential regions and stepped in others, as in the CPVS bath analysis method. It is usually advantageous to employ a plurality of potential cycles between fixed limits to provide a steady-state electrode surface, which typically yields more reproducible results. Steady-state is indicated by substantially equivalent voltammograms on successive cycles.

The reference electrode calibration of the present invention is readily performed during the normal course of CVS or CPVS plating bath analysis. For example, the test reference electrode may be calibrated relative to the zero current point between plating and stripping using the same voltammetric data generated to determine the stripping peak area $A_r(0)$ in the supporting electrolyte for the CVS or CPVS analysis. Since the plating bath analysis is typically performed under computer control, no additional equipment is needed to automatically perform the calibration of the present invention. Such automatic calibration of the reference electrode without removal from the plating equipment, which is enabled by the present invention, saves labor, time and expense, and minimizes errors in the plating bath analysis.

Further features and advantages of the invention will be apparent to those skilled in the art from the following detailed description, taken together with the accompanying drawings.

DETAILED DESCRIPTION OF THE INVENTION

Figure 1:
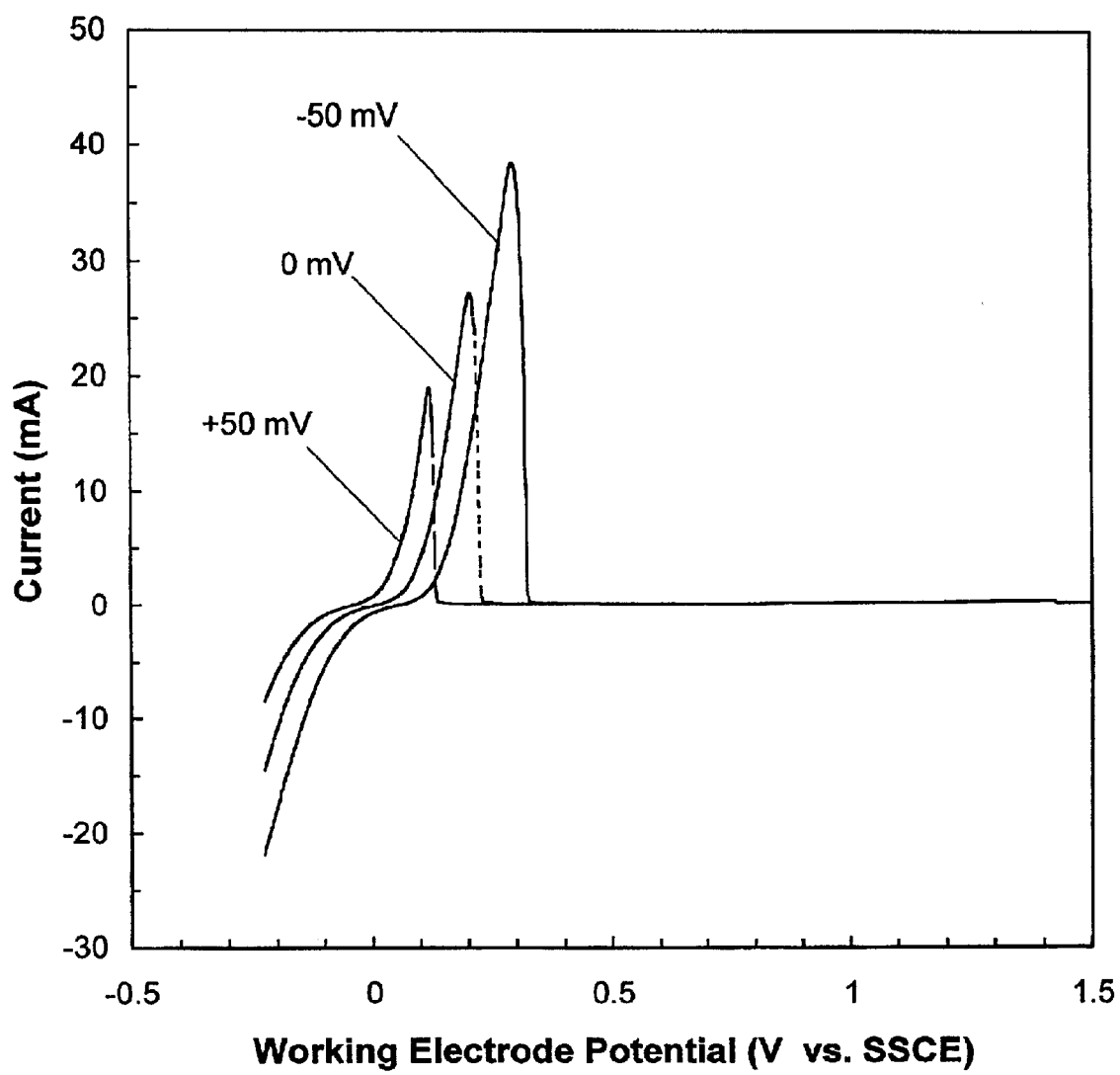
FIG. 1 shows the effect of reference electrode potential differences of $\pm 50$ mV on the anodic scans for steady-state cyclic voltammograms at 100 mV/s for a 4-mm diameter platinum rotating disk electrode (2500 rpm) in an acid copper sulfate supporting electrolyte.

Technical terms used in this application are generally known to those skilled in the art. The term "electrode potential", or simply "potential", refers to the voltage occurring across a single electrode-solution interface, whereas a "cell voltage" is the total voltage applied between two electrodes. As used in this application, the terms "electroplating" and "electrodeposition" are equivalent and the term "plating" encompasses both electroplating and electroless plating. A plating bath contains organic additives whose concentrations are controlled within ranges, whereas the corresponding "supporting electrolyte" has substantially the same inorganic composition but no organic additives, and a "background electrolyte" is the supporting electrolyte with known amounts of organic additives added. The term "plating solution" encompasses the terms "plating bath", "background electrolyte" and "supporting electrolyte". A "cyclic voltammogram" is a plot of current or current density (on the y-axis) versus the working electrode potential (on the x-axis) typically obtained by cycling the working electrode potential with time between fixed negative and positive limits. Voltammetric data may be generated by scanning the voltage at a constant rate or by stepping the voltage, or by a combination of potential scanning and stepping. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential.

According to the present invention, a test reference electrode used for voltammetric analysis of an electroplating bath is calibrated by monitoring the current while a time-dependent potential is applied to an inert working electrode relative to the reference electrode in the plating bath, or the supporting electrolyte or a background electrolyte thereof. The applied time-dependent potential encompasses a voltage range such that metal is plated onto the working electrode and then anodically stripped from the working electrode surface. The potential of the reference electrode is calibrated with respect to the potential of the working electrode at a predetermined stage in the current response for which the potential of the working electrode is substantially insensitive to variations in the plating solution composition and temperature. The composition of a plating solution normally varies because of solution preparation errors and batch to batch variations in the makeup solutions and chemicals. Since organic additives tend to strongly affect the current response to an applied potential, the test reference electrode calibration is preferably performed in the supporting electrolyte, which does not contain organic additives.

In practice, the working electrode potential corresponding to the predetermined stage in the current response is first measured relative to that of a standard reference electrode of known potential, which is typically a previously unused reference electrode. The difference in the working electrode potential measured subsequently under substantially the same conditions for the test reference electrode yields the offset or error in the potential of the test reference electrode compared to that of the standard reference electrode. This offset can be used to automatically correct the potential of the test electrode so that the working electrode is cycled between the same voltage limits during the voltammetric plating bath analysis. It is not necessary to repeat the measurement with the standard reference electrode for a given supporting electrolyte since the potential of the working electrode corresponding to the predetermined stage in the current response is constant. The same reference electrode can first be used as the standard reference electrode and subsequently as the test electrode with drift in its potential measured by the method of the present invention. The same plating solution composition is preferably employed for measurements with the standard reference electrode and the test reference electrode but plating solutions of different composition could be used.

The inert working electrode may be comprised of any suitable electrically conducting material that is stable in the plating solution under the conditions used for the reference electrode calibration but is preferably comprised of a noble metal, for example, platinum, iridium, gold, osmium, palladium, rhenium, rhodium, ruthenium, and alloys thereof. Other oxidation-resistant metals and alloys, stainless steel, for example, may also be used as working electrode materials. The suitability of a given electrode material may depend on the plating bath being analyzed and the measurement conditions.

Various configurations may be used for the working electrode but the rotating disk configuration is preferred. In this case, a disk of the electrode material is embedded flush with the end of an insulating cylinder, typically comprised of a plastic material (a halocarbon polymer, for example). The disk electrode is rotated in the plating solution to provide controlled hydrodynamic conditions at the electrode surface, which generally improves the reproducibility of the measurement results. The diameters of the disk and insulating cylinder may vary widely but are typically 3–5 mm for the disk and 10–20 mm for the insulating cylinder. The rotating disk electrode is usually rotated at a constant rate (100–5000 rpm) but the electrode rotation may be modulated with time. The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). If a stationary working electrode is used for the test reference electrode calibration of the present invention, the hydrodynamic conditions at the electrode surface are preferably controlled, by stirring or pumping the solution, for example.

The time-dependent potential may in some cases be applied directly between the working electrode and the reference electrode but is preferably applied by means of a counter electrode (typically used in conjunction with an electronic potentiostat) so as to avoid polarization of the reference electrode. The counter electrode may be comprised of an inert material or an active metal. Practically any electrical conductor that resists oxidation in the plating solution may be used as an inert counter electrode, including metals, alloys and conducting oxides (mixed titanium-ruthenium oxide, for example). A preferred counter electrode material is 316 stainless steel, which is highly oxidation-resistant and relatively inexpensive but other types of stainless steel or other oxidation-resistant alloys (inconel, for example) may also be used. Other suitable inert counter electrode materials include noble metals, for example, platinum, iridium, gold, osmium, palladium, rhenium, rhodium, ruthenium, and alloys thereof. A preferred active counter electrode material is the metal that is electroplated from the plating solution in which the reference electrode is calibrated. Depolarizers (sulfur or phosphorus, for example) may be included in the counter electrode active metal to facilitate dissolution of the metal so as to avoid breakdown of plating solution.

Various waveforms for the potential applied to the working electrode may be used. In a preferred embodiment, the working electrode potential is cycled at a constant scan rate (typically 10–500 mV/s) between fixed positive and negative potential limits, as in the CVS plating bath analysis method. The potential may also be stepped as a function of time, or may be scanned in some voltage regions and stepped in others, as in the CPVS plating bath analysis method. A wide variety of suitable potential waveforms will be apparent to those skilled in the art. A single potential cycle or a plurality of cycles may be used. Different time-dependent potentials may be applied to the working electrode for measurements with the standard and test reference electrodes if the potential for the predetermined stage in the current response is not substantially affected by the difference. For example, different potential scan limits might be used without substantially affecting the zero-current crossover between plating and stripping.

It is usually advantageous to repetitively cycle the potential of the working electrode between fixed negative and positive potential limits to provide a steady-state electrode surface, as indicated by substantially equivalent voltammograms or voltammetric features on successive cycles. This minimizes variations in the current caused by changes in the electrode surface state and improves the precision of the reference electrode calibration. Convergence to steady-state can be quantitatively monitored via key features of the voltammograms, for example, the integrated area under the stripping peak. In this case, steady state is indicated by successive stripping peak areas that differ by less than a predetermined percentage (0.5%, for example).

A preferred stage in the current response for reference electrode calibration according to the present invention is the zero-current crossover point from metal plating to metal stripping. The working electrode potential corresponding to this crossover point is readily measured and is relatively insensitive to variations in solution composition and temperature, and to variations in the potential limits and scan rate. Other stages in the current response that may be suitable for reference electrode calibration include the peak in the metal stripping current, a predetermined fraction of the peak metal stripping current, or a predetermined cathodic plating current. The optimum stage in the current response for reference electrode calibration may depend on the type of plating bath involved and the parameters used for voltammetric analysis.

This invention may be applied to calibration of reference electrodes used for voltammetric analysis of any plating bath for which the plated metal can be anodically stripped from an inert working electrode. Such baths include those for electroplating a variety of metals including copper, tin, lead, silver, cadmium, zinc, and alloys thereof, as well as those involving various anions and bath pH values, for example, acid copper sulfate, acid copper sulfamate, alkaline copper pyrophosphate, and alkaline copper cyanide. The invention may also be used to calibrate test reference electrodes used for voltammetric analysis of electroless plating baths.

This invention can be used to calibrate any type of reference electrode used for voltammetric plating bath analysis. Typical reference electrodes include silver—silver chloride (SSCE), saturated calomel (SCE), standard calomel, and mercury—mercury sulfate. In some systems, a metal in equilibrium with its ions in solution may be employed as a reference electrode ($Cu/Cu^{2+}$, for example). Reference electrodes may include a double solution junction or a gelled electrolyte to minimize solution mixing that might contaminate the plating bath or cause drift in the reference electrode potential.

The reference electrode calibration of the present invention may be performed using data generated during the normal course of CVS and CPVS plating bath analyses, which generally involve a step of cycling the potential of a rotating platinum disk electrode between fixed limits in the plating bath supporting electrolyte. For the plating bath analysis, this step conditions the electrode and provides a baseline stripping peak area $A_r(0)$ that is used to normalize stripping peak areas for plating solutions containing organic additives. In a preferred embodiment of the present invention, the test reference electrode used for the CVS or CPVS analysis is calibrated relative to the potential corresponding to the zero-current crossover between plating and stripping in the CVS or CPVS voltammetric data for the supporting electrolyte. The zero current crossover potential is first measured for a standard reference electrode. Differences in the zero-current crossover potential for subsequent measurements with the test reference electrode are used to correct the potential of the reference electrode for this offset. Since the plating bath analysis is typically performed under computer control, such reference electrode offset corrections can be made automatically via relatively simple changes in the computer software.

DESCRIPTION OF A PREFERRED EMBODIMENT

In a preferred embodiment, the reference electrode calibration of the present invention is performed using voltammetric data generated for a rotating platinum disk electrode in the plating bath supporting electrolyte during the normal course of CVS or CPVS plating bath analysis. The potential of this platinum working electrode is repetitively cycled relative to a reference electrode between fixed potential limits via a potentiostat and a counter electrode, which may be comprised of stainless steel, a noble metal, or the plated metal. The potential limits employed depend on the type of plating bath and may depend on the particular additive being analyzed. The steady-state working electrode potential corresponding to the zero-current crossover from plating to stripping is taken to be a constant. This potential is first measured relative to a standard reference electrode of known potential and subsequently for the test reference electrode, which may be the same electrode as the standard reference electrode. The potential of the test reference electrode is corrected for the offset corresponding to the difference in these two measured potentials so that errors in subsequent voltammetric measurements are minimized. Such corrections are preferably made automatically by the same computer used for the CVS or CPVS plating bath analysis. The frequency of the corrections depends on the rate of drift in the reference electrode potential. For double-junction SSCE reference electrodes in acid copper sulfate electroplating baths, calibration and correction are typically repeated every eight hours.

The voltammetric measurement parameters are preferably optimized with respect to the CVS or CPVS additive analysis since they are typically not critical to the reference electrode calibration. Key CVS measurement parameters and their typical ranges include the electrode rotation rate (100–10,000 rpm), potential scan rate (10–500 mV/s), negative potential limit (−0.05 to −0.5 V vs. SSCE) and positive potential limit (1.4 to 1.8 V vs. SSCE). Additional CPVS measurement parameters include the potentials and hold times for the pulses or steps used. Measurements should be made at constant solution temperature to minimize errors. For acid copper sulfate solutions, the temperature is maintained at 3° to 4° above room temperature. A suitable rotating disk electrode is comprised of a smooth platinum disk (4 mm diameter) embedded flush with the end of a Kel-F® plastic cylinder (13 mm diameter) by hot pressing.

The efficacy of the present invention was demonstrated via voltammetric measurements for a platinum disk electrode (4 mm diameter) rotating at 2500 rpm in a typical acid copper sulfate supporting electrolyte (25° C.) containing 75 g/L $CuSO_4.5H_2O$ (17.5 g/L $Cu^{2+}$), 175 g/L $H2SO_4$, and 50 ppm chloride ion (added as hydrochloric acid). The working electrode voltage was scanned at 100 mV/s between −0.225 V and +1.575 V vs. three different SSCE reference electrodes having potential offsets of 0 mV, +50 mV and −50 mV with respect to each other. The voltammetric measurements were made under potentiostatic control (stainless steel counter electrode) using a Qualilab QL-10 plating bath analyzer (ECI Technology, Inc.).

Figure 2:
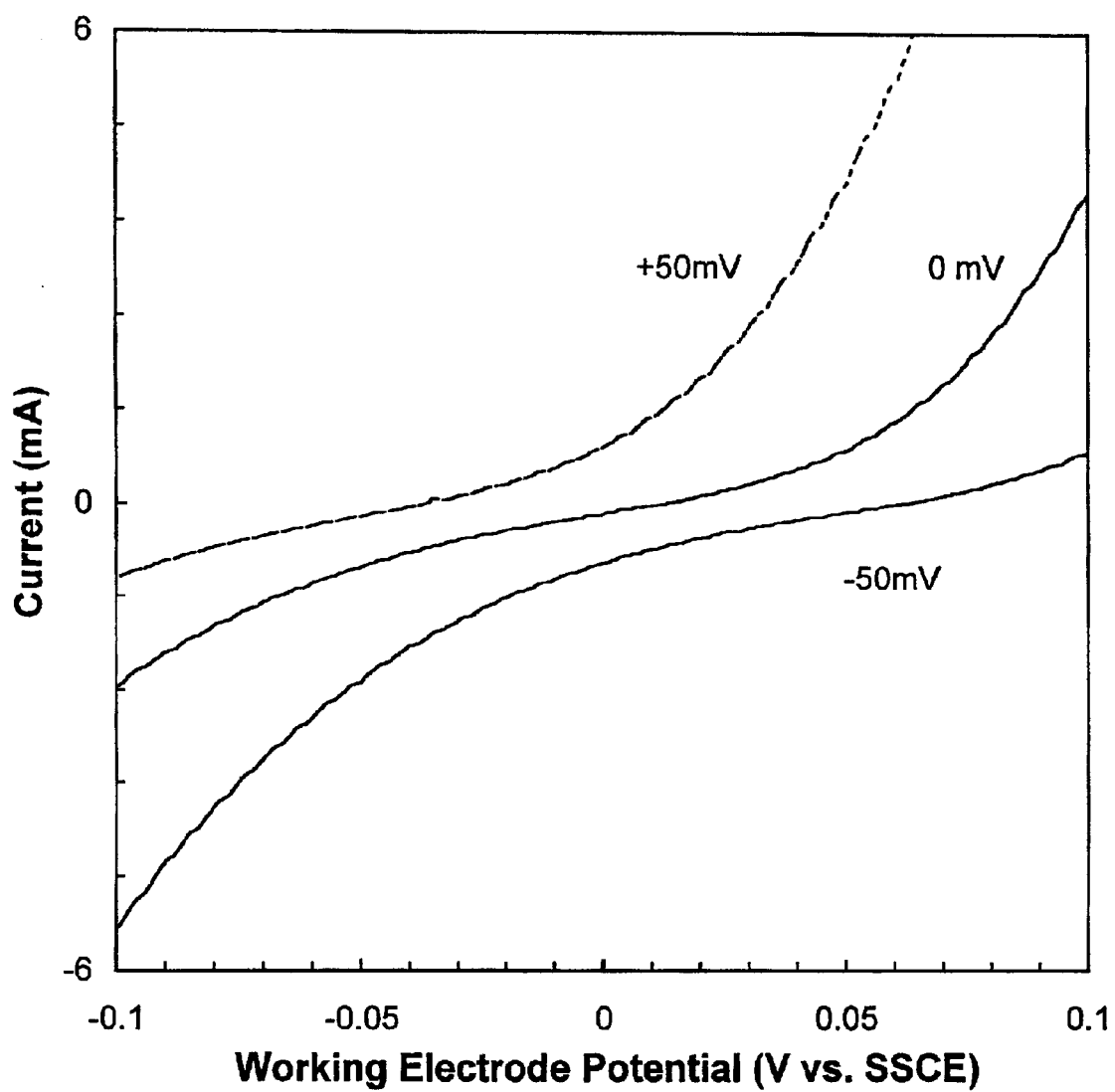
FIG. 2 shows the region around the zero-current crossing between metal plating and stripping for the voltammograms of FIG. 1 on an expanded scale.

FIGS. 1 and 2 show the positive scans (on different scales) for steady state voltammograms obtained with the three reference electrodes that had offsets of 0 mV, +50 mV and −50 mV with respect to each other. The cathodic currents correspond to electroplating of copper metal and the anodic current peaks correspond to stripping of the deposited copper metal from the platinum electrode surface. The zero-current crossover point between plating and stripping and the current peak are shifted to positive or negative potentials as expected for the reference electrode offsets. The zero-current crossover potentials and the calculated reference electrode offsets are tabulated in Table 1. Good agreement between the measured and calculated offsets is evident.

Table 2 and 3 illustrate the effects of variation in the supporting electrolyte composition and temperature on the zero-current crossover potential. Even for these relatively large variations in electrolyte composition ($\pm 25\%$) and temperature (10° C.), the zero-current crossover potential spans only a 13 mV range. In practice, variations in the supporting electrolyte composition and temperature are much smaller so that the method of the present invention provides calibration of the reference electrode used for voltammetric plating bath analysis with a precision of about one millivolt.

TABLE 1

Calibration Data for Three Reference Electrodes

| Reference Electrode Potential Offset (mV) | Zero-Current Crossover Potential (mV) | Calculated Offset (mV) |
|---|---|---|
| 0 | 13 | — |
| −50 | −36.5 | −49.5 |
| +50 | +62.5 | +49.5 |

TABLE 2

Effect of Supporting Electrolyte Composition on the Zero-Current Potential

| Copper Ion (g/L) | Sulfuric Acid (g/L) | Chloride Ion (ppm) | Zero-Current Crossing (mV) |
|---|---|---|---|
| 17.5 | 175 | 50 | 24 |
| 13.1 | 175 | 50 | 16 |
| 21.9 | 175 | 50 | 27 |
| 17.5 | 131 | 50 | 29 |
| 17.5 | 219 | 50 | 21 |
| 17.5 | 175 | 37.5 | 24 |
| 17.5 | 175 | 62.5 | 26 |

TABLE 3

Effect of Temperature on the Zero-Current Potential

| Temperature (° C.) | Zero-Current Crossing (mV) |
|---|---|
| 25 | 29 |
| 27.5 | 31 |
| 30 | 33 |
| 35 | 37 |

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for calibrating the potential of a test reference electrode used for voltammetric analysis of a plating bath, comprising the steps of:

measuring the current response to a time-dependent potential applied to a working electrode relative to a standard reference electrode in a plating solution such that metal is plated onto and then anodically stripped from the working electrode surface;

measuring the current response to the time-dependent potential applied to the working electrode relative to the test reference electrode in the plating solution; and comparing the working electrode potentials applied relative to the standard reference electrode and the test reference electrode at a predetermined stage in the current response to determine the difference in potential between the standard reference electrode and the test reference electrode.

2. The method of claim 1, wherein the standard and test reference electrodes are selected from the group consisting of silver—silver chloride, saturated calomel, standard calomel, and mercury—mercury sulfate.

3. The method of claim 1, wherein at least one of the reference electrodes includes a double junction.

4. The method of claim 1, wherein at least one of the reference electrodes includes a gelled electrolyte.

5. The method of claim 1, wherein the plating bath is of a type used to deposit a metal selected from the group consisting of copper, tin, lead, silver, cadmium, zinc, and alloys thereof.

6. The method of claim 1, wherein the plating solution is the supporting electrolyte of the plating bath.

7. The method of claim 1, wherein the working electrode is an inert metal selected from the group consisting of platinum, iridium, gold, osmium, palladium, rhenium, rhodium, ruthenium, and alloys thereof.

8. The method of claim 1, wherein the working electrode is a rotating disk electrode.

9. The method of claim 1, wherein the time-dependent potential is applied to the working electrode by means of a counter electrode.

10. The method of claim 9, wherein the counter electrode is comprised of stainless steel.

11. The method of claim 9, wherein the counter electrode is comprised of a noble metal selected from the group consisting of platinum, iridium, gold, osmium, palladium, rhenium, rhodium, ruthenium, and alloys thereof.

12. The method of claim 9, wherein the counter electrode is comprised of the same metal which is plated from the plating solution onto the working electrode.

13. The method of claim 1, wherein the potential applied to the working electrode is scanned at a constant rate as a function of time.

14. The method of claim 1, wherein the potential applied to the working electrode is stepped as a function of time.

15. The method of claim 1, wherein the time-dependent potential applied to the working electrode comprises a plurality of cycles between a fixed negative potential and a fixed positive potential.

16. The method of claim 1, wherein the predetermined stage in the current response is the zero-current point corresponding to the crossover from metal plating to metal stripping.

17. The method of claim 1, wherein the predetermined stage in the current response is the peak in the stripping current.

18. The method of claim 1, wherein the predetermined stage in the current response is a predetermined fraction of the peak in the stripping current.

19. The method of claim 1, wherein the predetermined stage in the current response is a predetermined cathodic current value.

20. A method for calibrating the potential of a test reference electrode used for voltammetric analysis of a plating bath, comprising the steps of:

measuring the current response to a time-dependent potential applied by means of a counter electrode to a working electrode relative to a standard reference electrode in a plating solution such that metal is plated onto and then anodically stripped from the working electrode surface;

measuring the current response to the time-dependent potential applied by means of a counter electrode to the working electrode relative to the test reference electrode in the plating solution; and comparing the working electrode potentials applied relative to the standard reference electrode and the test reference electrode at the zero-current point corresponding to the crossover from metal plating to metal stripping to determine the difference in potential between the standard reference electrode and the test reference electrode.

21. A method for calibrating the potential of a test reference electrode used for voltammetric analysis of a plating bath, comprising the steps of:

(1) measuring the current response to a time-dependent potential applied to a working electrode relative to a test reference electrode in a plating solution such that metal is plated onto and then anodically stripped from the working electrode surface;

(2) repeating step (1) at a later time; and (3) comparing the working electrode potentials applied in steps (1) and (2) at a predetermined stage in the current response to determine the change in the potential of the test reference electrode with time.

22. A method for calibrating the potential of a test reference electrode used for voltammetric analysis of a plating bath, comprising the steps of:

measuring the current response to a first time-dependent potential applied to a working electrode relative to a standard reference electrode in a first plating solution such that metal is plated onto and then anodically stripped from the working electrode surface;

measuring the current response to a second time-dependent potential applied to the working electrode relative to the test reference electrode in a second plating solution such that metal is plated onto and then anodically stripped from the working electrode surface; and comparing the working electrode potentials applied relative to the standard reference electrode and the test reference electrode at a predetermined stage in the current response to determine the difference in potential between the standard reference electrode and the test reference electrode.

* * * * *